United States Patent
Pearson

(10) Patent No.: US 6,308,718 B1
(45) Date of Patent: Oct. 30, 2001

(54) COCKTAIL PICK AND CANOPY

(76) Inventor: John L. Pearson, 232 Spruce St., Apt. B, Arroyo Grande, CA (US) 93420

( * ) Notice: Subject to any disclaimer, the term of this patent is extended or adjusted under 35 U.S.C. 154(b) by 0 days.

(21) Appl. No.: 09/684,509

(22) Filed: Oct. 6, 2000

(51) Int. Cl.[7] .................................................. A61C 15/02
(52) U.S. Cl. ........................................... 132/329; 366/129
(58) Field of Search ..................................... 366/129, 342, 366/343; 416/69, 70 R, 71; 132/321, 329; 135/15.1, 98, 99, 118; 40/317, 324, 637; D3/5, 6, 7, 17; D7/300.2, 376, 671, 688, 689

(56) References Cited

U.S. PATENT DOCUMENTS

| | | | |
|---|---|---|---|
| 343,079 | * | 6/1886 | Smith . |
| D. 411,762 | | 7/1999 | You . |
| D. 375,025 | * | 10/1996 | Barton . |
| 1,512,090 | | 10/1924 | Hirtz . |
| 1,774,909 | * | 9/1930 | Wells . |
| 2,103,948 | * | 12/1937 | Jones . |
| 2,327,077 | * | 8/1943 | Teetor . |
| 2,462,991 | * | 3/1949 | Palinkas . |
| 2,510,551 | * | 6/1950 | Cardillo . |
| 2,637,537 | * | 5/1953 | Ernst . |
| 2,651,315 | * | 9/1953 | Witty . |
| 2,717,463 | | 9/1955 | Sindler . |
| 2,723,111 | | 11/1955 | Lawrence . |
| 2,793,842 | * | 5/1957 | Bacon . |
| 3,109,634 | * | 11/1963 | Anson . |
| 3,488,769 | * | 1/1970 | Falkenberg . |
| 3,772,809 | | 11/1973 | Schneller . |
| 4,483,622 | | 11/1984 | Muhi et al. . |
| 5,386,840 | * | 2/1995 | Lane ..................... 132/329 |
| 5,568,973 | * | 10/1996 | Gorab ................... 366/129 |
| 5,713,664 | * | 2/1998 | Harilela ................ 366/129 |
| 5,761,819 | * | 6/1998 | Ledy-Gurren ........ 366/129 |
| 6,056,206 | * | 5/2000 | Whiton ................. D7/300.2 |

FOREIGN PATENT DOCUMENTS

2671332 * 7/1992 (FR) ..................................... 366/129

* cited by examiner

*Primary Examiner*—Charles E. Cooley

(57) ABSTRACT

A cocktail pick and canopy for dressing up beverages and provide a toothpick for a meal. The cocktail pick and canopy includes a pick member having a tapered bottom end and a bulbous top end for being removably disposed in a beverage glass; and also includes a canopy member having at least one slit in a center thereof for receiving the pick member therethrough and also having a plurality of creases extending radially from a center thereof.

14 Claims, 2 Drawing Sheets

COCKTAIL PICK AND CANOPY

BACKGROUND OF THE INVENTION

1. Field of the Invention

The present invention relates to drink glass pick and canopy and more particularly pertains to a new cocktail pick and canopy for dressing up beverages and provide a toothpick for a meal.

2. Description of the Prior Art

The use of a drink glass pick and canopy is known in the prior art. More specifically, a drink glass pick and canopy heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. Des. 350,643; U.S. Pat. No. 2,717,463; U.S. Pat. No. 2,723,111; U.S. Pat. No. 3,772,809; U.S. Pat. No. 1,512,090; and U.S. Pat. No. 4,48 3,622.

While these devices fulfill their respective, particular objectives and requirements, the aforementioned patents do not disclose a new cocktail pick and canopy. The inventive device includes a pick member having a tapered bottom end and a bulbous top end for being removably disposed in a beverage glass; and also includes a canopy member having at least one slit in a center thereof for receiving the pick member therethrough and also having a plurality of creases extending radially from a center thereof.

In these respects, the cocktail pick and canopy according to the present invention substantially departs from the conventional concepts and designs of the prior art, and in so doing provides an apparatus primarily developed for the purpose of dressing up beverages and provide a toothpick for a meal.

SUMMARY OF THE INVENTION

In view of the foregoing disadvantages inherent in the known types of drink glass pick and canopy now present in the prior art, the present invention provides a new cocktail pick and canopy construction wherein the same can be utilized for dressing up beverages and provide a toothpick for a meal.

The general purpose of the present invention, which will be described subsequently in greater detail, is to provide a new cocktail pick and canopy which has many of the advantages of the drink glass pick and canopy mentioned heretofore and many novel features that result in a new cocktail pick and canopy which is not anticipated, rendered obvious, suggested, or even implied by any of the prior art drink glass pick and canopy, either alone or in any combination thereof.

To attain this, the present invention generally comprises a pick member having a tapered bottom end and a bulbous top end for being removably disposed in a beverage glass; and also includes a canopy member having at least one slit in a center thereof for receiving the pick member therethrough and also having a plurality of creases extending radially from a center thereof.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new cocktail pick and canopy which has many of the advantages of the drink glass pick and canopy mentioned heretofore and many novel features that result in a new cocktail pick and canopy which is not anticipated, rendered obvious, suggested, or even implied by any of the prior art drink glass pick and canopy, either alone or in any combination thereof.

It is another object of the present invention to provide a new cocktail pick and canopy which may be easily and efficiently manufactured and marketed.

It is a further object of the present invention to provide a new cocktail pick and canopy which is of a durable and reliable construction.

An even further object of the present invention is to provide a new cocktail pick and canopy which is susceptible of a low cost of manufacture with regard to both materials and labor, and which accordingly is then susceptible of low prices of sale to the consuming public, thereby making such cocktail pick and canopy economically available to the buying public.

Still yet another object of the present invention is to provide a new cocktail pick and canopy which provides in the apparatuses and methods of the prior art some of the advantages thereof, while simultaneously overcoming some of the disadvantages normally associated therewith.

Still another object of the present invention is to provide a new cocktail pick and canopy for dressing up beverages and provide a toothpick for a meal.

Yet another object of the present invention is to provide a new cocktail pick and canopy which includes a pick member having a tapered bottom end and a bulbous top end for being removably disposed in a beverage glass; and also includes a canopy member having at least one slit in a center thereof for receiving the pick member therethrough and also having a plurality of creases extending radially from a center thereof.

Still yet another object of the present invention is to provide a new cocktail pick and canopy that can be conveniently used for advertising.

Even still another object of the present invention is to provide a new cocktail pick and canopy that adds a decorative touch to one's meal.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
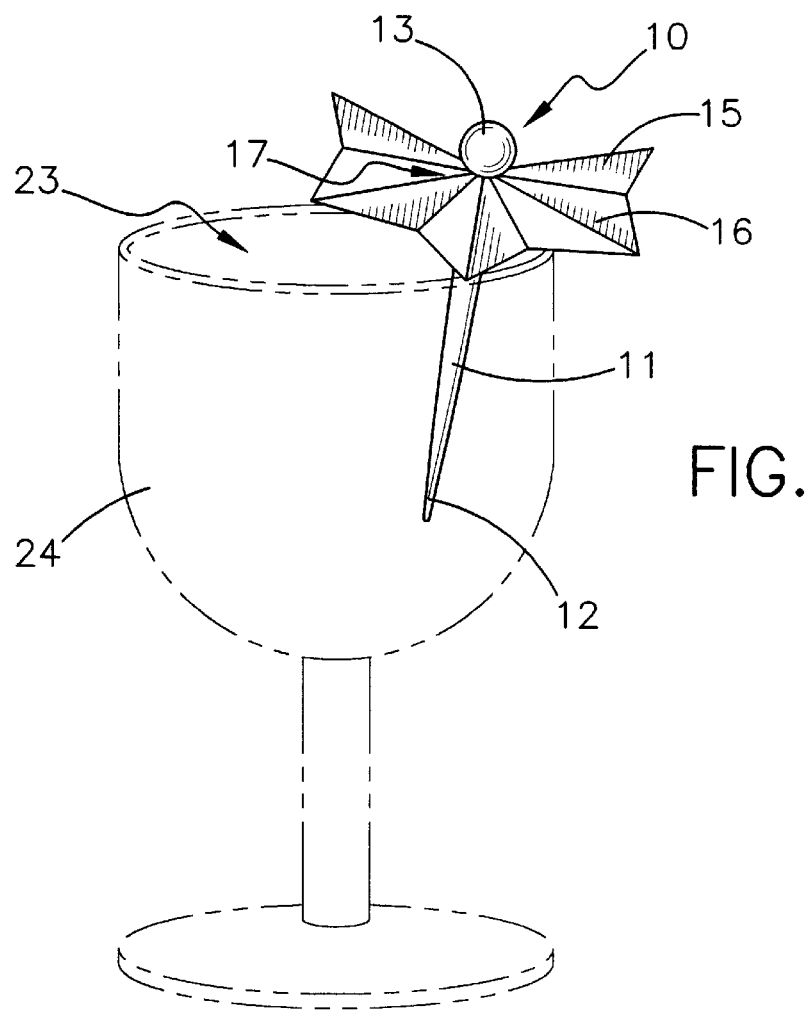
FIG. 1 is a perspective view of a new cocktail pick and canopy according to the present invention and shown in use.
Figure 2:
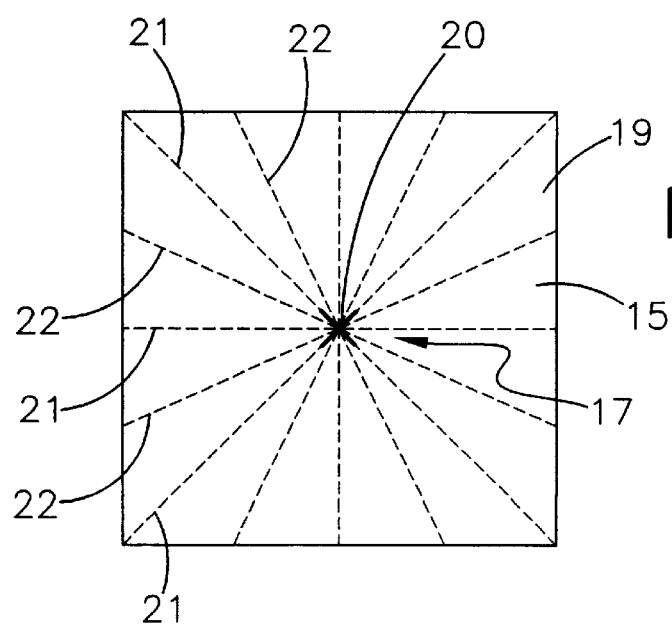
FIG. 2 is a top plan view of the non-folded canopy member of the present invention.
Figure 3:
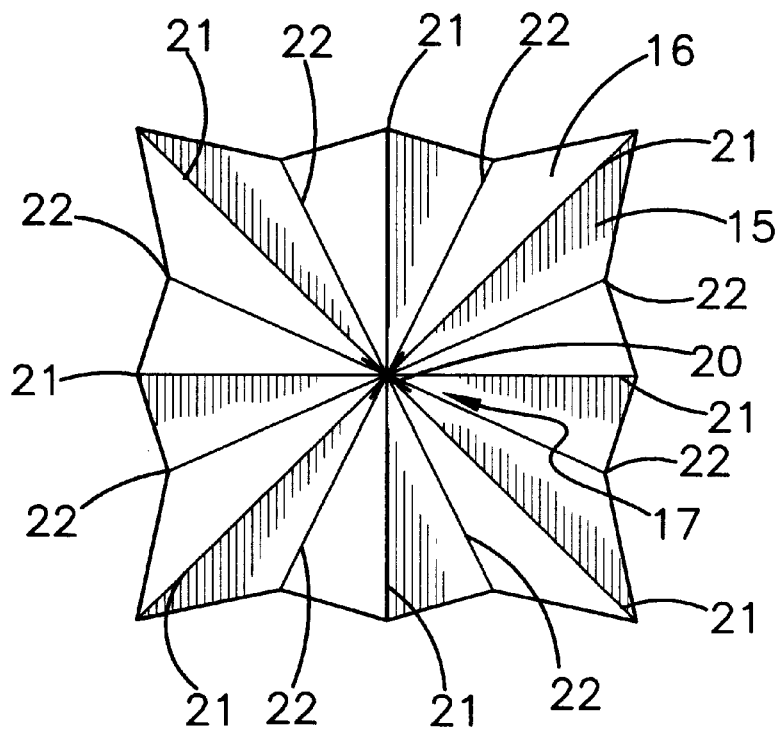
FIG. 3 is a top plan view of the creased canopy member of the present invention.
Figure 4:
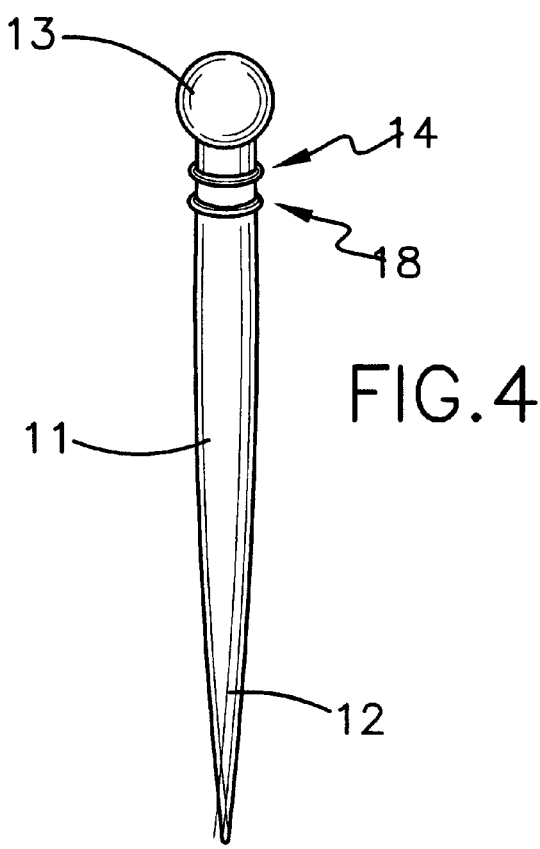
FIG. 4 is a perspective view of the pick member of the present invention.

With reference now to the drawings, and in particular to FIGS. 1 through 4 thereof, a new cocktail pick and canopy embodying the principles and concepts of the present invention and generally designated by the reference numeral 10 will be described.

As best illustrated in FIGS. 1 through 4, the cocktail pick and canopy 10 generally comprises a pick member 11 having a tapered bottom end 12 and a bulbous top end 13 for being removably disposed in a beverage glass 24. The cocktail pick and canopy 10 also includes a canopy member 15 having at least one slit 20 in a center 17 thereof for receiving the pick member 11 therethrough and also having a plurality of creases 21,22 extending radially from the center 17 thereof. The pick member 11 further includes a pair of circumferentially-extending ribs 14 being spaced apart and being securely and integrally disposed upon a wall and near the top end 13 thereof with the ribs being adapted to securely receive and retain the canopy member 15 therebetween. The canopy member 15 includes a top side 16 and a bottom side 19 and a plane within which the center 17 is disposed. The creases 21,22 include first creases 21 and second creases 22 which are folded in a direction opposite to the first creases 21 with the first creases 21 essentially forming radially-extending vertexes and the second creases 22 essentially forming radially-extending valleys. The vertexes 21 are generally equally spaced about the canopy member 15 with each valley 22 being disposed between a respective pair of adjacently-disposed vertexes 21. The valleys 22 are generally equally spaced about the canopy member 11. The second creases 22 are angled below the plane and the first creases 21 are angled above the plane with the canopy member 15 being essentially made of paper and capable of being folded and unfolded along the creases 21,22 and with the canopy member 15 being approximately 49 square millimeters.

In use, the user would unfold the canopy member 15 into the first and second creases 21,22 and then would insert the pick member 11 through the at least one slit 20 in the center 17 of the canopy member 15 with the canopy member 15 being received and retained between the ribs 14. The cocktail pick and canopy 10 would be used in conjunction with a beverage 23 with the pick member 11 being disposed within the container 24 and the canopy member 15 resting upon the rim of the container 24 such as glass.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A cocktail pick and canopy comprising:
  a pick member having a tapered bottom end and a bulbous top end for being removably disposed in a beverage;
  a canopy member having at least one slit in a center thereof for receiving said pick member therethrough and also having a plurality of creases extending radially from a center thereof;
  wherein said pick member further includes a pair of circumferentially-extending ribs being spaced apart and being disposed upon a wall and near said top end thereof, said ribs being adapted to securely receive and retain said canopy member therebetween; and
  wherein said canopy member includes a top side and a bottom side and a plane within which said center of said canopy member is disposed, said creases including first creases and second creases which are folded in a direction opposite to said first creases.

2. A cocktail pick and canopy as described in claim 1, wherein said first creases essentially form radially-extending vertexes and said second creases essentially form radially-extending valleys.

3. A cocktail pick and canopy as described in claim 2, wherein said vertexes are generally equally spaced about said canopy member with each said valley being disposed between a respective pair of adjacently-disposed said vertexes.

4. A cocktail pick and canopy as described in claim 2, wherein said valleys are generally equally spaced about said canopy member.

5. A cocktail pick and canopy as described in claim 1, wherein said canopy member is essentially made of paper and can be folded and unfolded along said creases.

6. A cocktail pick and canopy as described in claim 1, wherein said first creases are angled above said plane and said second creases are angled below said plane.

7. A cocktail pick and canopy comprising:

a pick member having a tapered bottom end and a bulbous top end for being removably disposed in a beverage; and a canopy member having at least one slit in a center thereof for receiving said pick member therethrough and also having a plurality of creases extending radially from said center thereof, said pick member further including a circumferentially-extending groove disposed in a wall and near said top end thereof, said groove being adapted to securely receive and retain said canopy member, said canopy member including a top side and a bottom side and a plane within which said center is disposed, said creases including first creases and second creases which are folded in a direction opposite to said first creases, said first creases essentially forming radially-extending vertexes and said second creases essentially forming radially-extending valleys, said vertexes being generally equally spaced about said canopy member with each said valley being disposed between a respective pair of adjacently-disposed said vertexes, said valleys being generally equally spaced about said canopy member, said second creases being angled below said plane and said first creases being angled above said plane, said canopy member being essentially made of paper and capable of being folded and unfolded along said creases, said canopy member being approximately 49 square millimeters.

8. A cocktail pick and canopy comprising:

a pick member having a tapered bottom end and a bulbous top end for being removably disposed in a beverage;

a canopy member having at least one slit in a center thereof for receiving said pick member therethrough and also having a plurality of creases extending radially from a center thereof; and wherein said canopy member includes a top side and a bottom side and a plane within which said center of said canopy member is disposed, said creases including first creases and second creases which are folded in a direction opposite to said first creases.

9. A cocktail pick and canopy as described in claim 8, wherein said pick member further includes a pair of circumferentially-extending ribs being spaced apart and being disposed upon a wall and near said top end thereof, said ribs being adapted to securely receive and retain said canopy member therebetween.

10. A cocktail pick and canopy as described in claim 8, wherein said first creases essentially form radially-extending vertexes and said second creases essentially form radially-extending valleys.

11. A cocktail pick and canopy as described in claim 10, wherein said vertexes are generally equally spaced about said canopy member with each said valley being disposed between a respective pair of adjacently-disposed said vertexes.

12. A cocktail pick and canopy as described in claim 10, wherein said valleys are generally equally spaced about said canopy member.

13. A cocktail pick and canopy as described in claim 8, wherein said canopy member is essentially made of paper and can be folded and unfolded along said creases.

14. A cocktail pick and canopy as described in claim 8, wherein said first creases are angled above said plane and said second creases are angled below said plane.

* * * * *